United States Patent [19]

Calisi

[11] Patent Number: 4,508,103

[45] Date of Patent: Apr. 2, 1985

[54] PRESSURE MONITORING INTERCONNECT SYSTEM

[76] Inventor: Constance M. Calisi, 5518 Martel, Dallas, Tex. 75206

[21] Appl. No.: 529,382

[22] Filed: Sep. 6, 1983

[51] Int. Cl.³ .............................................. A61B 5/02
[52] U.S. Cl. ..................................... 128/673; 128/748
[58] Field of Search ............................... 128/672–673, 128/675, 748; 73/700; 137/625.29, 625.42

[56] References Cited

U.S. PATENT DOCUMENTS

| | | | |
|---|---|---|---|
| 3,122,136 | 2/1964 | Murphy, Jr. | 128/673 |
| 3,581,733 | 6/1971 | Grandjean | 128/673 |
| 3,610,228 | 10/1971 | Temkin | 128/673 X |
| 4,300,571 | 11/1981 | Waldbillig | 128/673 |
| 4,428,383 | 1/1984 | De Vroom | 128/748 |
| 4,444,198 | 4/1984 | Petre | 128/673 |

*Primary Examiner*—Lee S. Cohen
*Assistant Examiner*—Angela D. Sykes
*Attorney, Agent, or Firm*—Kanz, Scherback & Timmons

[57] ABSTRACT

Disclosed is a bypass valve interconnect system for connecting two lumens of a multi-lumen catheter to a single transducer for alternately measuring and recording fluid pressure in each lumen. The system includes a three-way stopcock valve interposed in each lumen output line and interconnected through a bypass line.

6 Claims, 2 Drawing Figures

PRESSURE MONITORING INTERCONNECT SYSTEM

BACKGROUND OF THE INVENTION

This invention relates to methods and apparatus for continuous and/or intermittent monitoring of central venous and pulmonary artery pressures. More particularly, it relates to methods and apparatus for selectively interconnecting the pressure monitoring output ports of a multi-lumen catheter to a single pressure monitoring apparatus, such as a transducer or the like, so that a single pressure monitoring apparatus may be used to selectively monitor pressures in a plurality of locations by simple switching of selector valves.

Various therapeutic and diagnostic tools have recently been developed to assist in monitoring of body functions and conditions and in treatment of critically ill patients. Although many of such tools may appear to be of simple design, their use often requires complex and expensive electronic apparatus to interpret and record the functions monitored and further requires highly trained staff personnel for proper safe and effective use. Typical of such diagnostic tools is the Swan-Ganz catheter. This apparatus comprises a multi-lumen catheter designed and adapted for insertion into the right ventricle through the right atrium and, when properly used, can monitor blood temperature, pulmonary artery pressure and even pulmonary capillary wedge pressure. In various modifications, the apparatus can be used for direct solution injection to determine cardiac output by thermodilution and may incorporate electrodes for ventricular pacing, atrial pacing, atrioventricular sequential pacing and recording intra-atrial and intraventricular electrograms. Such catheters are considered invaluable aids in treating critically ill patients, such as those with complications following acute myocardial infarctions, as well as to monitor cardiac and pulmonary status and maintain fluid balance in patients in shock, congestive heart failure and various other critical conditions.

In the typical arrangement, a multi-lumen catheter is positioned with a lumen opening at the distal end thereof within the right ventricle or pulmonary artery and a second lumen opening in the right atrium. These lumens are then appropriately externally interconnected with pressure-responsive apparatus to monitor pulmonary artery pressure and central venous pressure, respectively.

Since the pulmonary artery pressure is generally the more critical pressure and is sufficiently high to require the use of complex monitoring apparatus such as electro-mechanical or electronic pressure transducers to accurately continuously monitor and record, the output port of the distal lumen is generally connected to a transducer and recording apparatus. The central venous pressure is, of course, somewhat lower. Accordingly, it is common practice to connect the output port of the atrial lumen to a simple water manometer rather than a second transducer, primarily because of cost and equipment availability considerations. While this arrangement is quite cost-effective and generally acceptable, it suffers many disadvantages. For example, transducer-recorded pressures are generally recorded and/or displayed in standard units of millimeters of mercury while the units displayed on a water monometer indicate millimeters of water. Thus attending personnel are required to make a mathematical conversion to record both pressures in equivalent standard units. While the mathematical conversion is quite simple, it is obviously subject to inadvertent human error. More importantly, reading the level of a liquid miniscus is subject to error and obviously quite subjective. Furthermore, accuracy of measurement is dependent upon location of the base reference point with respect to the patient. This not only requires a highly subjective decision on the part of the operator, but may vary widely from operator to operator and with physical movement of the patient. Thus, for these and other reasons, pressure measurement taken using a monometer are generally not reliable as precision measurements.

While it is apparent that a transducer could be used to measure pressures in both output ports, simple economics and equipment availability usually prohibit the use of dual transducers and recording apparatus on one patient.

SUMMARY OF THE INVENTION

In accordance with the present invention, an interconnect bypass system is provided whereby a single transducer may be used to selectively intermittently monitor pressures in two output ports of a single multi-lumen catheter. The bypass interconnect system is interconnected adjacent the catheter output ports with any solution injection valves intermediate the bypass system and the pressure monitoring equipment. In its simplest embodiment, the bypass interconnect system comprises a pair of interconnected three-way rotary stopcock valves disposed parallel in the lumen output lines with their respective third ports interconnected. Thus any injection fluids must pass through the stopcock valves and the valves may be switched as desired to permit direct measurements of pressures appearing at the output ports thereof without cross-feeding of solutions. The system of the invention not only eliminates most of the likelihood of human error in measuring and recording pressures, but by using the same transducer and recording apparatus for measurement of all pressures, any error inherent in the equipment will be constant so that differences in pressures will be precisely measured and immediately apparent without interpolation or mathematical conversion.

Other features and advantages of the invention will become more readily understood from the following detailed description taken in conjunction with the appended claims and attached drawings in which:

DETAILED DESCRIPTION OF THE INVENTION

Figure 1:
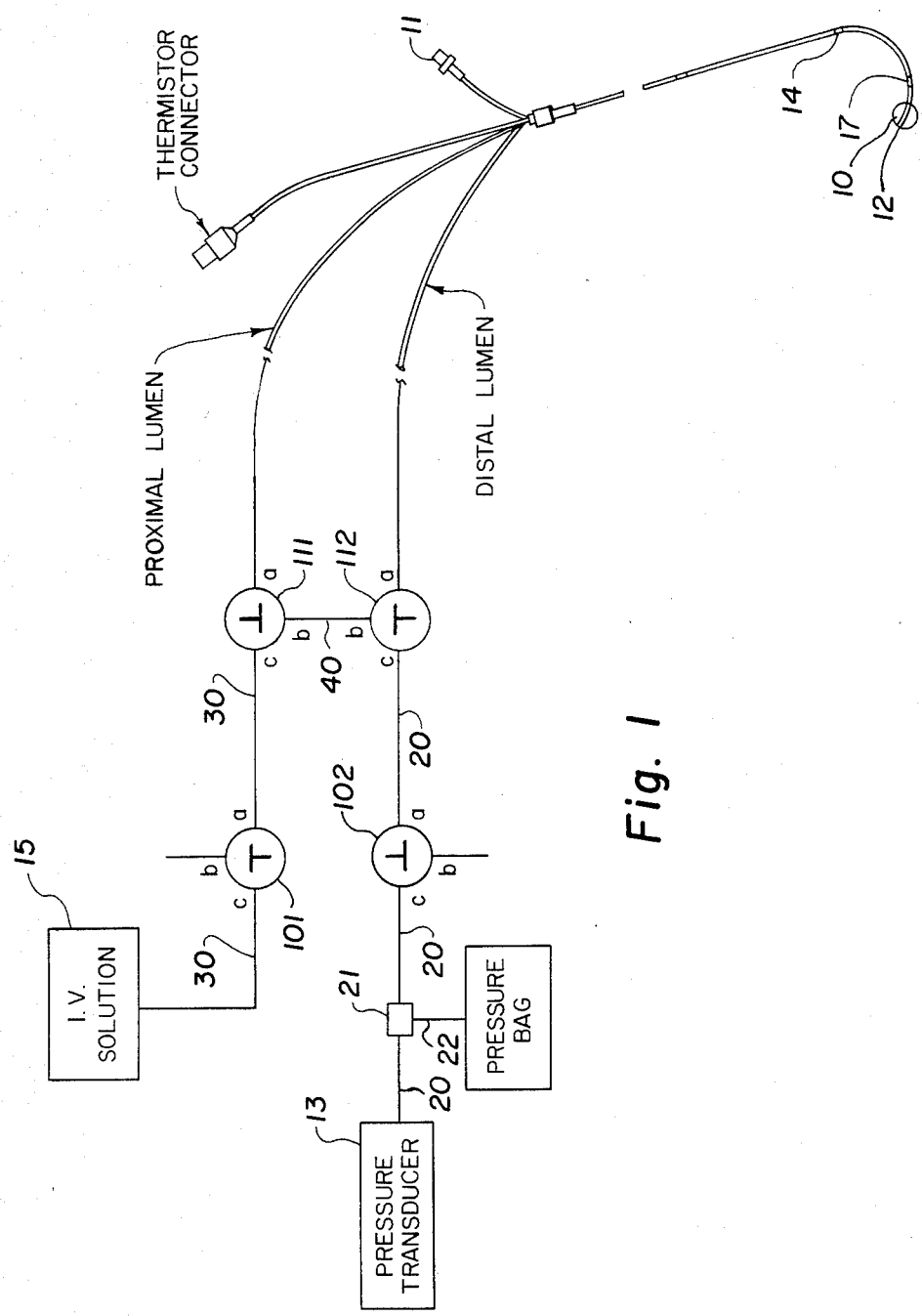
FIG. 1 is a schematic illustration of the preferred embodiment of the invention when arranged to measure pressure in the distal lumen opening of a multi-lumen catheter.
Figure 2:
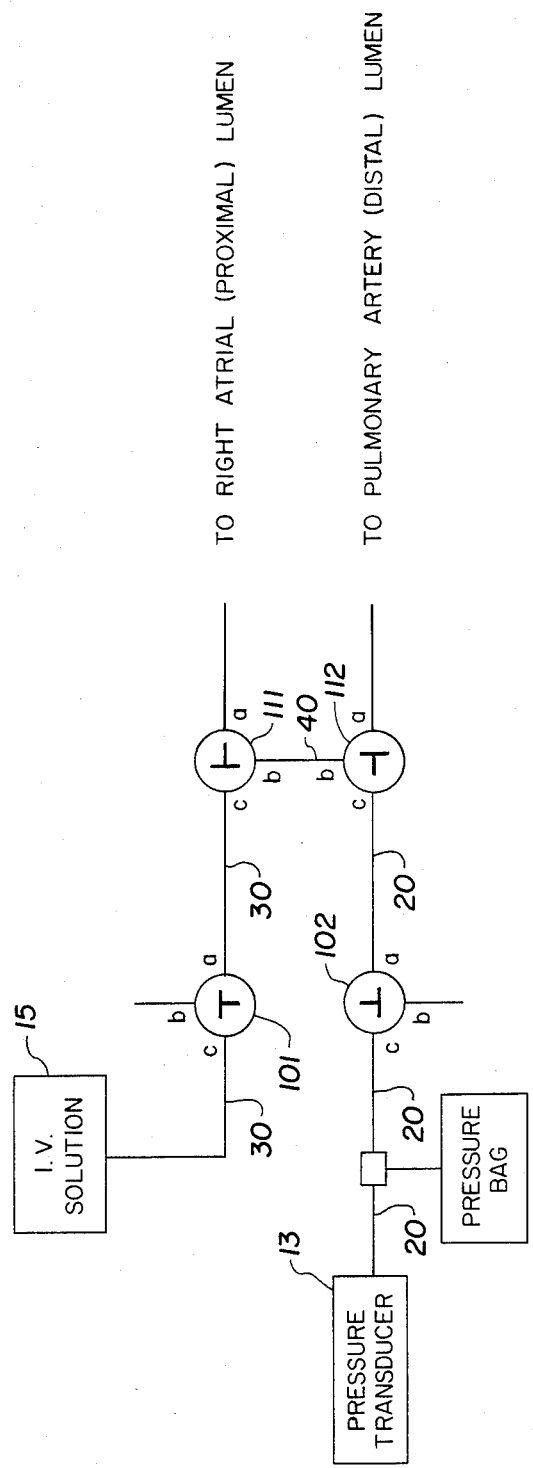
FIG. 2 is a schematic illustration of the same apparatus when the stopcock valves have been switched to permit measurement of the pressure in the proximal lumen.

As illustrated in FIGS. 1 and 2, the preferred embodiment of the invention comprises a plurality of interconnected rotary stopcock valves interconnecting a multi-lumen catheter and conventional pressure monitoring equipment. A typical Swan-Ganz multi-lumen catheter is illustrated in FIG. 1 which carries an inflatable balloon 10 at the end thereof connected to balloon inflation/deflation means 11 through one of the lumens. The catheter is inserted through the right atrium and right ventricle into the pulmonary artery. The lumen opening 12 at the distal end of the catheter will be in communication with blood in the pulmonary artery. This lumen (hereinafter referred to as the pulmonary artery lumen) is connected to an electronic or electromechanical transducer 13 as hereinafter described so that the fluid pressure appearing at the distal lumen opening 12 is measured directly by the transducer 13.

As is well known by those skilled in the art, the catheter is inserted into the right atrium and the balloon 11 inflated. The catheter then follows the blood flow through the tricuspid valve into the right ventricle and through the semilunar valve into the pulmonary artery. With the balloon inflated, the distal end of the catheter continues to follow blood flow until it reaches a branch of the pulmonary artery with a smaller diameter than that of the balloon at which point it wedges in the vessel. With the balloon 10 wedged in a branch of the pulmonary artery, the opening at the distal end thereof is downstream and thus no longer in contact with pulmonary artery pressure but only with pulmonary capillary wedge pressure. Thus, pulmonary capillary wedge pressure may be measured intermittently by inflating the balloon. Upon deflation of the balloon the pulmonary artery pressure again appears at the distal lumen opening 12. With the catheter in this position, the opening 14 of a third lumen (hereinafter referred to as the proximal lumen opening) is situated within the right atrium. Pressure monitoring apparatus appropriately connected to the proximal lumen may therefore continuously or intermittently measure central venous pressure.

The catheter may contain other lumens for other purposes. For example, a typical Swan-Ganz catheter ordinarily includes at least a fourth lumen which carries connecting leads to a thermistor situated at the open end 17 thereof and positioned to determine blood temperature as illustrated in FIG. 1. However, since the invention is directed primarily to apparatus for measurement of pressures appearing at the distal lumen opening 12 and the proximal lumen opening 14, further description of the operation and various embodiments of the Swan-Ganz or other multi-lumen catheters is unnecessary herein.

As illustrated in FIGS. 1 and 2, the pulmonary artery lumen is connected to a pressure transducer 13 through conduit 20. In conventional arrangements a three-way stopcock valve 102 is interconnected in conduit 20 intermediate the pulmonary artery lumen and the pressure transducer 13 and an interflow valve 21 disposed in conduit 20 between valve 102 and pressure transducer 13. Arm 22 of interflow valve 21 is connected to a pressure bag. As it is well known to those skilled in the art, a suitable flush solution, such as a heparin solution or the like, is maintained in the pressure bag at a pressure greater than any pressure which could appear at the distal lumen opening and the interflow valve 21 adjusted so that the flush solution flows into conduit 20 at a very low rate, typically about 3 cc/hr. In this manner, conduit 20 between the transducer 13 and the patient remains filled with flush solution while the blood pressure appearing at the distal lumen opening 14 is transmitted directly to the transducer 13.

In normal operation the three-way spool of valve 102 is rotated to interconnect ports A and C of valve 102, thus providing a direct connection in conduit 20. Port B of the valve is ordinarily connected to injection or infusion means so that the valve spool may be selectively rotated to permit injection of other solutions directly into the conduit 20 as desired.

In similar fashion, the proximal lumen is connected to an I.V. solution bag 15 through conduit 30. A three-way stopcock valve 101 is interconnected in conduit 30 intermediate the proximal lumen and the I.V. solution bag 15. In normal operation the three-way spool of valve 101 is rotated to interconnect ports A and C of valve 101 and port B connected to other injection or infusion means as desired.

Prior to the invention disclosed herein, multi-lumen catheters were conventionally interconnected as disclosed hereinabove without including stopcock valves 111 and 112 and substituting a water manometer for the I.V. solution bag 15. Thus pressure appearing at the proximal lumen opening 14 could be measured using the water manometer and pressure appearing at the distal lumen opening 12 would be measured by the pressure transducer 13. In accordance with the invention, stopcock valves 111 and 112 are inserted in the apparatus in the arrangement disclosed in FIGS. 1 and 2. In the arrangement of FIG. 1, the spool of valve 111 is rotated to interconnect ports A and C, thus providing a direct line connection of the proximal lumen with conduit 30 and isolating bypass line 40. Likewise, the spool of valve 112 is rotated to connect ports A and C to provide direct connection of the distal lumen and line 20 and likewise isolating bypass line 40. In this arrangement the pressure appearing at the distal lumen opening 12 is directly measured and recorded with pressure transducer 13 in conventional fashion. However, to obtain a reading of pressure appearing at the proximal lumen opening 14, the spool of valve 112 is rotated to isolate the pulmonary artery lumen and connect conduit 20 to line 40 through ports B and C of valve 112. The spool of valve 111 is rotated to interconnect ports A and B, thus interconnecting bypass line 40 with the proximal lumen while isolating line 30 leading to the I.V. solution bag 15. This arrangement is illustrated in FIG. 2. It will be observed that in the arrangement of FIG. 2 the pressure at the proximal lumen opening 14 appears at the pressure transducer 13 and such pressure may be directly recorded by the pressure measuring and recording apparatus 13.

It will be observed that bypass line 40 is connected into the system only when taking pressure readings at the proximal lumen opening 14. At all other times bypass line 40 is completely isolated between valves 111 and 112 as illustrated in FIG. 1. Thus the apparatus may be used in conventional manner in the arrangement illustrated in FIG. 1 to monitor pressure appearing at the distal lumen opening 12 and only temporarily or intermittently switched to the arrangement shown in FIG. 2 to temporarily or intermittently measure the pressure appearing at the proximal lumen opening 14. It will be further observed that the system at all times remains entirely closed, thus totally avoiding any possibility of contamination or the like. Furthermore, the inaccuracies inherent in the use a water manometer to measure pressures are totally eliminated and a single pressure-sensing and recording instrument is used to record all pressures. The possibility of human errors inherent in converting measurement units are thereby eliminated.

While elimination of the manometer for pressure readings is a particularly unique advantage of the system of the invention, it will be observed that the only addition to the conventional system is the inclusion of two relatively inexpensive rotary stopcock valves and an interconnecting bypass line 40. The additional cost of apparatus employing the invention with respect to prior art arrangements is therefore minimal and operation of the apparatus of the invention is so simple that relatively minor training is required to permit the nursing staff to properly use the apparatus.

Various modifications of the bypass arrangement will be readily apparent to those skilled in the art. For example, various other types of valves may be used and additional valves may be arranged in similar configurations to permit intermittent measurement of pressures at more than two lumens of a multi-lumen catheter. Accordingly, it will be observed that the principles of the invention may practiced and embodied in various forms. It is to be understood, therefore, that while the invention has been described with particular reference to specific embodiments thereof, the forms of the invention shown and described in detail are to be taken as preferred embodiments of same. Various changes and modifications may be resorted to without departing from the spirit and scope of the invention as defined by the appended claims.

What is claimed:

1. Fluid pressure monitoring apparatus comprising:
   (a) a catheter including at least a first lumen having an opening at a first location and a second lumen having an opening at a second spaced apart location on said catheter;
   (b) pressure measuring means;
   (c) first conduit means connecting said pressure-measuring means with said first lumen;
   (d) solution injection means;
   (e) second conduit means connecting said solution injection means and said second lumen; and
   (f) valve and bypass means interconnected between said first and second conduit means operable to selectively interconnect said pressure-measuring means in fluid communication with said second lumen through said valve and bypass means while isolating said first lumen and said solution injection means.

2. Apparatus as defined in claim 1 wherein said valve and bypass means comprises:
   (i) a first rotary stopcock valve with first, second and third ports, the first port connected to said first lumen and the third port connected to said pressure-measuring means;
   (ii) a second rotary stopcock valve with first, second and third ports, the first port connected to said second lumen and the third port connected to said solution injection means; and
   (iii) bypass means connecting said second port of said first valve and said second port of said second valve.

3. Apparatus as defined in claim 2 further including:
   (iv) a third rotary stopcock valve connected between said first rotary stopcock valve and said pressure-measuring means; and
   (v) a fourth rotary stopcock valve connected between said second rotary stopcock valve and said solution injection means.

4. In combination with a multi-lumen catheter having at least a first lumen and a second lumen and first and second conduits connected to said first and second lumens, respectively, an interconnect system comprising:
   (a) a bypass line;
   (b) means for connecting said first conduit in fluid communication with said bypass line while interrupting fluid communication between said first conduit and said first lumen; and
   (c) means for connecting said second lumen in fluid communication with said bypass line while interrupting fluid communication between said second lumen and said second conduit.

5. Apparatus for interconnection with a multi-lumen catheter having at least first and second lumens and pressure measuring means comprising:
   (a) a first valve having first, second and third ports with said first port adapted for connection with said first lumen;
   (b) a second valve having first, second and third ports with said first port adapted for connection with said second lumen;
   (c) a third valve having first, second and third ports with the first port thereof connected to the third port of said first valve and the third port thereof adapted for connection to said pressure measuring means;
   (d) a fourth valve having at least first and second ports with the first port thereof connected to said third port of said second valve; and
   (e) bypass means connected between the second port of said first valve and said second port of said second valve.

6. The method of independently monitoring fluid pressures within at least two lumens of a multi-lumen catheter with a single pressure monitoring means comprising the steps of:
   (a) connecting the first port of a first valve having first, second and third ports in fluid communication with said first lumen;
   (b) connecting the first port of a second valve having first, second and third ports in fluid communication with said second lumen;
   (c) connecting the second port of said first valve with the second port of said second valve;
   (d) connecting the third port of said first valve to said pressure monitoring means;
   (e) selectively alternately connecting said first lumen in fluid communication with said pressure monitoring means by switching said first valve to connect said first port thereof with said third port thereof and isolating said second port thereof; and
   (f) selectively alternately connecting said second lumen in fluid communication with said pressure monitoring means by switching said first valve to connect said second port thereof with said third port thereof while isolating said first port thereof and switching said second valve to connect said first port thereof with said second port thereof while isolating said third port thereof.

* * * * *